United States Patent
Tian et al.

(10) Patent No.: US 11,135,170 B2
(45) Date of Patent: Oct. 5, 2021

(54) SOLID FORMULATION

(71) Applicant: ENESI PHARMA LIMITED, Abingdon (GB)

(72) Inventors: Wei Tian, Abingdon (GB); Richard Zajicek, Abingdon (GB)

(73) Assignee: ENESI PHARMA LIMITED, Abingdon (GB)

(*) Notice: Subject to any disclaimer, the term of this patent is extended or adjusted under 35 U.S.C. 154(b) by 0 days.

(21) Appl. No.: 15/769,514

(22) PCT Filed: Oct. 20, 2016

(86) PCT No.: PCT/GB2016/053276
§ 371 (c)(1),
(2) Date: Apr. 19, 2018

(87) PCT Pub. No.: WO2017/068351
PCT Pub. Date: Apr. 27, 2017

(65) Prior Publication Data
US 2018/0311168 A1 Nov. 1, 2018

(30) Foreign Application Priority Data
Oct. 20, 2015 (GB) .................................... 1518594

(51) Int. Cl.
*A61K 9/20* (2006.01)
*A61K 38/26* (2006.01)
*A61K 38/29* (2006.01)
*A61K 38/31* (2006.01)
*A61K 9/00* (2006.01)

(52) U.S. Cl.
CPC .......... *A61K 9/2054* (2013.01); *A61K 9/0021* (2013.01); *A61K 9/0024* (2013.01); *A61K 9/205* (2013.01); *A61K 9/2009* (2013.01); *A61K 9/2013* (2013.01); *A61K 9/2018* (2013.01); *A61K 9/2095* (2013.01); *A61K 38/26* (2013.01); *A61K 38/29* (2013.01); *A61K 38/31* (2013.01)

(58) Field of Classification Search
None
See application file for complete search history.

(56) References Cited

U.S. PATENT DOCUMENTS

2007/0010440 A1* 1/2007 Schense ............ A61K 38/1875
514/8.8
2013/0012916 A1 1/2013 Labeur et al.

FOREIGN PATENT DOCUMENTS

| WO | WO 94/22423 A1 | 10/1994 |
| WO | WO 96/03978 A1 | 2/1996 |
| WO | WO 96/07397 A2 | 3/1996 |
| WO | WO 96/08289 A1 | 3/1996 |
| WO | WO 01/26602 A1 | 4/2001 |
| WO | WO 02/100380 A1 | 12/2002 |
| WO | WO 03/023773 A1 | 3/2003 |
| WO | WO 03/051328 A1 | 6/2003 |
| WO | WO 2004/014468 A1 | 2/2004 |
| WO | WO 2004/075875 A1 | 9/2004 |
| WO | WO 2006/082439 A1 | 8/2006 |
| WO | WO 2008/102136 A2 | 8/2008 |
| WO | WO 2011/087496 A1 | 7/2011 |
| WO | WO 2011/098518 A2 | 8/2011 |

OTHER PUBLICATIONS

Zhang et al. "Development and Testing of Solid Dose Formulations Containing Polysialic Acid Insulin Conjugate: Next Generation of Long-Acting Insulin", Journal of Diabetes Science and Technology, vol. 4, May (Year: 2010).*
Aug. 3, 2016 Combined Search & Examination Report issued in GB 1518594.5.
Feb. 2, 2017 International Search Report & Written Opinion issued in PCT/GB2016/053276.

* cited by examiner

*Primary Examiner* — Isis A Ghali
(74) *Attorney, Agent, or Firm* — Nixon & Vanderhye P.C.

(57) ABSTRACT

A solid dosage form for injection and a method of making said dosage form wherein the dosage form has a moisture content of 5% (w/w) or less. The solid dosage form comprises a dried matrix including a first excipient and 0.01 to 50% (w/w) or more than 50% and up to 80% (w/w) of a therapeutic peptide; and one or more additional excipients and at least 5% (w/w) of CMC, based on the total weight of the solid dosage form, wherein the dosage form has a width of 0.5 mm to 2 mm.

18 Claims, No Drawings

SOLID FORMULATION

This application is the U.S. national phase of International Application No. PCT/GB2016/053276 filed 20 Oct. 2016, which designated the U.S. and claims priority to GB Patent Application No. 1518594.5 filed 20 Oct. 2015, the entire contents of each of which are hereby incorporated by reference.

FORMULATION

The present invention relates to solid dosage forms for parenteral delivery of therapeutic peptides. In particular the solid dosage forms comprise the excipient carboxymethylcellulose (CMC) which increases the strength, for example, compressive strength of the formulation. The solid dosage forms have sufficient strength to penetrate the skin of a subject without the use of a needle or cannula.

BACKGROUND

Several publications and patent documents are referenced in this application in order to more fully describe the state of the art to which this invention pertains. The disclosure of each of these publications and documents is incorporated by reference herein.

Injection of aqueous solutions of pharmaceuticals using a needle and syringe is the most common method for delivery of pharmaceuticals by the parenteral route. This delivery route is used particularly for drugs such as protein biologicals and therapeutic peptides that would ordinarily be poorly absorbed using other routes, destroyed in the stomach or where rapid delivery is required.

However, over one third of drugs listed in the U.S. Pharmacopoeia and about 50% of new drug molecules are insoluble and therefore cannot easily be formulated for delivery with a needle and syringe or for transdermal drug delivery. As a result, many drugs currently have a sub-optimal formulation and many otherwise promising compounds never reach the market.

Therefore, solid forms of drugs have been developed to attempt to overcome the short-comings of aqueous delivery by needle and syringe.

WO94/022423 (Bukh Meditec) discloses bodies of a solid pharmaceutical composition having a shape and/or strength to enable penetration of unbroken skin or mucosa of a human or an animal to deliver an active substance, for example, a peptide. The bodies are exemplified by compositions comprising the excipients gelatine, agarose and gellan. There is no mention of the use of carboxymethylcellulose.

WO96/08289 (SCRAS) discloses 'toothpick' shaped rods for parenteral administration having a crush strength of 8 millipoise [sic]. The application discloses the use of conventional methods of manufacture but does not specifically discuss the techniques or refer to the use of carboxymethylcellulose to provide structural integrity.

WO96/03978 (Quadrant Holdings) discloses 'glassy' or vitreous solid dosage forms for parenteral administration. The dosage forms are prepared by heating compositions to high temperatures sufficient for melting and the formation of an amorphous, non-crystalline matrix.

WO01/26602 (Novo Nordisk) discloses an alternative method for producing elongate drug formulations for parenteral administration. The application discloses that an alternative production process using high compression forces is required to impart satisfactory strength to such formulations. There is no disclosure of the use of excipients alone to impart mechanical strength.

WO03/051328 (Novo Nordisk) discloses compositions for parenteral administration comprising water-impermeable coatings to control rate of release of active constituents.

WO03/023773 (Caretek Medical Limited, now Glide Pharmaceutical Technologies Limited) discloses the use of solid rods or splinters of a therapeutic compound for parenteral drug delivery. The application further discloses the use of 'pioneer projectiles' to facilitate drug delivery via the parenteral route. The document does not disclose the use of carboxymethylcellulose to increase mechanical strength.

WO2004/075875 (Alkabello A/S) discloses non-compressed fast-dispersing solid dosage forms comprising a saccharide matrix for oromucosal administration.

WO2008/102136 (Glide Pharmaceutical Technologies Ltd) discloses elongate bodies and solid formulations for parenteral injection. The document does not disclose the use of carboxymethylcellulose to increase mechanical strength.

EP2533814 (Ablynx NV and Glide Pharmaceutical Technologies Limited) discloses formulations for administration of immunoglobulin variable domains which can be solid. The document does not disclose the use of carboxymethylcellulose, in a formulation with additional excipients, to increase mechanical strength.

The use of such solid dosage forms for parenteral drug delivery has several advantages over other delivery forms. However, whilst the use of drug rods and splinters generally as small as, or smaller than, a grain of rice is advantageous, there is a trade-off with the amount of therapeutic peptide that can be incorporated whilst maintaining the requisite strength for skin penetration. Skin thickness and strength varies from one region of the body to another. Similarly, the thickness, hardness, moisture content and composition of underlying subcutaneous tissue will also vary, depending on sex, location on the body or age for example. Therefore, whilst some solid dosage formulations, particularly those with higher levels of peptide, may be able to penetrate the skin in some areas, they may not be able to be parenterally administered in others where they are required.

Thus, there is a need for solid dosage forms that enable a range of proportions of therapeutic peptides to be incorporated whilst maintaining or having an increased compressive strength for skin penetration, thereby enabling reliable delivery of the therapeutic peptide.

SUMMARY OF THE INVENTION

The inventors have made the surprising discovery that the addition of the excipient carboxymethylcellulose (CMC) to solid dosage formulations, especially when the formulation is substantially dry, produces solid dosage forms that have sufficient strength for parenteral administration.

Thus, in a first aspect of the invention there is provided a solid dosage form for injection having a moisture content of 5% (w/w) or less, the solid dosage form comprising: a dried matrix including a first excipient and 0.01 to 50% (w/w) of a therapeutic peptide; and one or more additional excipients and at least 5% (w/w) of CMC, based on the total weight of the solid dosage form, wherein the dosage form has a width of 0.5 mm to 2 mm.

In some embodiments, depending on the nature of the therapeutic peptide, the solid dosage forms of the invention may comprise a total of 0.5 to 30% (w/w) of therapeutic peptide, for example, 0.7 to 15% (w/w) or 0.8 to 10% (w/w), based on the total weight of the solid dosage form. Alternatively, the solid dosage forms of the invention may comprise higher levels of therapeutic peptide, for example 30 to 50% (w/w) or 40 to 50% (w/w), based on the total weight of the solid dosage form.

Further, even higher levels of therapeutic peptide are envisaged and have been shown to be possible, for example in relation to octreotide or liraglutide. In some cases, the solid dosage form comprises a higher percentage of a therapeutically effective peptide, for example more than 50% (w/w) and up to 80% or more preferably more than 50% and up to 72% (w/w) or more than 50% and up to 60% (w/w).

Thus, in a further aspect of the invention, there is provided a solid dosage form for injection having a moisture content of 5% (w/w) or less, the solid dosage form comprising: a dried matrix including a first excipient and 50 to 80% (w/w) of a therapeutically effective peptide; and one or more additional excipients and at least 5% (w/w) of CMC, based on the total weight of the solid dosage form. Preferably, the dosage form has a width of 0.5 mm to 2 mm.

The solid dosage forms of the invention comprise at least 5% (w/w) of CMC excipient, for example, 5 to 90% (w/w), 5 to 70% (w/w), 5 to 60% (w/w), 5 to 40% (w/w), more particularly 10 to 30% (w/w), based on the total weight of the solid dosage form. Particular amounts of CMC include 5% (w/w), 7% (w/w), 10% (w/w), 15% (w/w), 20% (w/w), 25% (w/w), 30% (w/w), 35% (w/w), 40% (w/w), 45% (w/w), 50% (w/w), 55% (w/w), 60% (w/w), 65% (w/w), 70% (w/w), 75% (w/w), 80% (w/w), 85% (w/w), 90% (w/w), based on the total weight of the solid dosage form.

Preferably, the one or more additional excipients is a bulking agent. The bulking agent may be selected from one or more of the following: polyol, for example, mannitol or sorbitol; sugars, for example, dextran or sucrose; and amino acids.

Particularly preferred is when the bulking agent is mannitol.

The solid dosage form may further comprise one or more excipients selected from the group comprising surfactants, sugars, amino acids, EDTA and stabilising agents.

The solid dosage forms may comprise a total of from 50 to 99.99% by weight of excipient(s), including CMC.

The term "therapeutic peptide" is used to refer to any physiologically or pharmaceutically active peptide that can be delivered from the solid dosage form via the parenteral route to produce a localised or systemic therapeutic effect in a human or animal.

The key classes of therapeutic peptides include somatostatins, vasopressins, platelet aggregate inhibitors, calicitonins, incretin hormones including glucagon-like peptides, and GNRH/LHRH agonists.

The solid dosage forms of the present invention are therefore useful in the treatment or prevention of diseases or disorders which are treated/prevented by the administration of therapeutic peptides including, but not limited to, those described above.

Preferably, the therapeutic peptide consists of 100 amino acid monomers or less, for example, 5 to 60 amino acids monomers, preferably 8 to 45 amino acid monomers.

Alternatively, the therapeutic peptides described herein may include chemically modified peptides, for example, peptides modified by acetylation, PEGylation, methylation, hydroxylation and albumin modification. Other examples of chemical modifications will be known to those skilled in the art.

The therapeutic peptide may be octreotide. Octreotide is used to treat severe diarrhea and other symptoms that occur with certain intestinal tumours or metastatic carcinoid tumours. Octreotide is also used to treat acromegaly.

Alternatively, the therapeutic peptide may be parathyroid hormone (PTH) or a fragment thereof such as PTH 1-34, also known as teriparatide, which is a synthetic or recombinant human 1-34 amino acid N terminal sequence of parathyroid hormone. PTH 1-34 is used to treat solitary bone cysts and hypoparathyroidism.

Alternatively, the therapeutic peptide may be exenatide or liraglutide which are glucagon-like peptide-1 receptor agonists, binding to the same receptors as the endogenous metabolic hormone GLP-1 that stimulates insulin secretion. Such peptides maybe used to treat diabetes mellitus type 2.

The term, "parenteral delivery" as used herein means that the solid dosage form is administered through the skin. Parenteral delivery includes subcutaneous and intramuscular administration, for example.

It will also be apparent that the solid dosage forms described herein may also be administered intradermally, i.e. into the skin rather than entirely through it, or through a mucous membrane.

The solid dosage forms of the invention may also be administered by surgery or trocar.

The solid dosage forms may be produced by extrusion. Alternatively, the solid dosage forms may be produced by moulding or forming. The solid dosage forms may also be produced by a combination of extrusion and moulding or extrusion and forming or extrusion and cutting. Alternatively, the dosage forms may be produced by granulation or lyophilisation.

In certain embodiments the solid dosage forms are sterilised by ionising irradiation, for example, electron beam or gamma irradiation. Alternatively, the components of the formulation are aseptically processed prior to formation of the solid dosage forms.

According to a second aspect of the invention there is provided drug delivery devices or packaged drugs for use with a drug delivery device which comprises solid dosage forms according to the first aspect.

According to a third aspect of the invention there is provided a solid dosage form according to the first aspect for use in the treatment of a disease or disorder in a subject, wherein the disease or disorder is treatable by parenteral administration of a therapeutic peptide including but not limited to those described above.

In a further aspect, the present invention provides use of a solid dosage form as described herein for the manufacture of a medicament for the treatment of one or more of conditions treatable by the parenteral administration of a therapeutic peptide including but not limited to those described above.

In a further aspect, the present invention provides a method of treatment of one or more conditions treatable by the therapeutic peptides mention above which comprises administering to a subject a solid dosage form of the disclosure.

The term "treatment" is intended to embrace prophylaxis as well as therapeutic treatment. Treatment of conditions or disorders also embraces treatment of exacerbations thereof.

DETAILED DESCRIPTION

The prevalence of injection phobia, generally defined in terms of ability to receive an injection, has been estimated to be between 7% and 22% in the general population and poses a serious challenge for healthcare providers. The physical sensation of a prick with a needle and syringe injection is followed by the sensations of the volume of fluid being pushed in and the needle being withdrawn. Usually each step of administration is also visible.

In terms of administration efficiency, following administration, solid dosage forms enable 100% of an active material to be bioavailable. In contrast, there is always some level of wastage with a needle and syringe, at least a quantity of the active material being left behind in the syringe. This allows needle-less technology to be used for high cost drugs where minimum wastage of the active drug is desired.

The use of solid dosage forms administered as needle-free or needleless injections is therefore advantageous since they are much quicker to administer than traditional needle and syringe. In the context of the present invention, a generalised feature of the solid dosage forms is that they are able to penetrate the skin of a subject in their own right, replacing the requirement for a needle. Essentially the solid dosage form takes the place of the needle.

In terms of skin sensation felt during needle and syringe injection, this is primarily due to the size of needle required and the large volume of liquid administered.

In a Phase I clinical trial the sensation felt during administration of a solid dosage form prepared by the Applicants was found to be equivalent to the sensation felt during skin penetration with a 27-gauge needle (one of the standard needle sizes commonly used for vaccinations). However, following this sensation the needleless injection was over almost instantly because the device pushes the solid dosage form into the skin very rapidly.

Solid dosage forms and compositions of the present invention preferably have a maximum diameter or width of 2 mm at their widest part. Particularly the width is less than 2 mm, less than 1 mm, particularly between 0.50 to 0.90 mm, for example, between 0.80 and 0.90 mm. Preferably, the width is 0.85 mm with a tolerance of ±5%. As a result of this it has been determined that such solid dosage forms can be injected essentially without or with very little sensation. If the diameter of the solid dosage forms is too small then they become very fragile and difficult to handle as well as not being sufficiently strong to penetrate skin.

Whilst the compositions may be manufactured in any length for most applications, the length of the dosage form, preferably a rod shaped dosage form, is particularly less than 15 mm, less than 10 mm, less than 8 mm and yet more particularly less than 6 mm, for example from 2 to 6 mm, in particular 4 mm. Preferably, the length of the solid dosage form is 4 mm with a tolerance of ±5%.

However, such small scale solid dosage forms are limited in the quantity of active material that they can contain. For example, currently very thin solid dosage forms would require a very long composition in order to contain the predetermined amount of active material. This also reduces the compressive strength of the composition and may cause it to break on administration. Thus, the dimensions of current solid dosage forms is determined by the dose of the active material and the quantity of excipients required to provide sufficient strength required for skin penetration.

Use of the term "strength" is meant that the composition has sufficient compressive strength to penetrate the skin of a human or animal. It has been determined experimentally that a pressure force of at least 80 MPa is required to reliably penetrate the epidermis of a human being with the claimed composition. This specification was arrived at by calculating that the mean pressure force minus $3\sigma$ (i.e. three standard deviations) should equal at least 80 MPa. Therefore, compositions for parenteral injection must be able to withstand such pressure force.

Compressive strength may be tested on a Shimadzu tensile testing machine. Tests are carried out by formulating the composition as a dosage form in the shape of a rod and applying a pressure force to the dosage form. The pressure force is increased until the dosage form breaks. The instrument records the pressure force necessary to crush the dosage form. This parameter is termed the compressive strength and should be understood as the breaking strength under compression. The tests must be carried out on dosage forms which are substantially dry.

Solid dosage forms of the present invention are able to withstand a pressure force of at least 80 MPa, for example, at least 100 MPa, at least 120 MPa, at least 130 MPa, or at least 140 MPa. Typically measurements are taken on formulations with a diameter of approx 0.85 mm. Typically measurements are taken on solid dosage forms of approximately 2 mm to ensure that results are comparable between formulations.

The inventors have made the surprising discovery that solid dosage forms containing CMC have a compressive strength that is higher than expected, especially when the dosage forms are substantially dry.

Use of the term "substantially dry" is meant that the solid dosage form has minimal levels of moisture in the formulation. The moisture content in the final solid dosage may be 5% (w/w) or less, preferably 3% (w/w) or less, more particularly, between 1 and 5% (w/w), between 1 and 3% (w/w), preferably between 2 and 3% (w/w), based on the total weight of the solid dosage form. Methods for analysing the moisture content in the final dosage form will be known to the skilled person. Suitable methods include thermogravimetric analysis (TGA), Karl Fisher (KF) and infrared analysis. The moisture present in the solid dosage may be water. A substantially dry dosage form can be achieved by subjecting the solid dosage form to convection drying, for example using a Memmert UF750 convention oven or equivalent, followed by vacuum drying, for example using a Memmert VO500 vacuum oven or equivalent. Other methods of drying will be known to the skilled person, for example, by drying the CMC prior to forming the solid dosage form. The other materials present in the dosage form may also be dried prior to mixing. The moisture present in the solid dosage form is integral to the formulation and is not considered a discrete active ingredient. For this reason, moisture, or water, is not listed as an ingredient in the exemplified formulations which list only the ratio of ingredients used to prepare the solid dosage forms. Water can be introduced prior to extruding, in order to form a paste for ease of extrusion. This moisture is then dried off as detailed herein. Also as mentioned herein, the level of moisture in the final product can be measured as a % (w/w) based on the total weight of the solid dosage form. It will be understood therefore that when referring to a % (w/w) of moisture, this is not a quantity of ingredient used to make the dosage form but a means of quantifying the level of moisture in the solid dosage form. Therefore, the solid dosage forms described herein will include therapeutic peptide, CMC, one or more additional excipients and a certain amount of moisture.

The dosage forms of the present invention are preferably stable in the sense that they do not significantly change after manufacture with respect to physical and chemical properties, e.g. potency of active, mechanical robustness and organoleptical properties like visual appearance of the dosage form.

Stability of a solid dosage form in order to ensure a sufficient shelf life of the final product may be measured with reference to the physical and/or chemical properties of the solid dosage form or its individual constituents. With most injectable dosages that are delivered through a needle and syringe the formulation is stored in a liquid. However, many drugs and vaccines are not sufficiently stable in a liquid formulation even if they are stored in a refrigerator. In these cases the drug is then stored as a powder and reconstituted with a diluent (typically water, saline or buffer) immediately before the injection. This process is complicated and in some emergency cases, such as with glucagon for the treatment of hypoglycaemia, there are cases where the patient or carer has injected the diluents without including the active drug.

Storing the formulations in a solid dosage form can provide enhanced shelf stability, avoid the need for cold chain storage and may provide an extended shelf life. Excipients can be added to provide enhanced stability beyond just transforming a formulation from a solution to a solid. The solid dose formulations may have enhanced stability against thermal degradation as well as enhanced stability to withstand degradation from ionising radiation such as during sterilisation.

The term "excipient" may include binders, disintegrants, glidants, lubricants, preservatives, sorbents and vehicles. Preferred excipients used in combination with CMC include: polyol, for example, mannitol and sorbitol; sugars, for example, dextran and sucrose; surfactants; sugars; amino acids; EDTA and stabilising agents. The solid dosage forms described herein may comprise mannitol in combination with CMC. Dextran may also be used in combination with both mannitol and CMC.

The solid dosage forms of the invention may comprise octreotide as the therapeutic peptide. The octreotide solid dosage form will further comprise CMC and one or more of the additional excipients described herein. For example, the solid dosage form may comprise between 1 and 50% (w/w) of octreotide, in particular 1 and 10% (w/w), preferably 2 to 5% (w/w) of octreotide, in addition to 20 to 40% (w/w), preferably 30 to 40% (w/w) of CMC, and 40 to 80% (w/w), preferably 50 to 70% (w/w) of one or more additional excipients. Alternatively, the solid dosage form may comprise more than 50% (w/w) and up to 80% of octreotide or more preferably more than 50% (w/w) and up to 72% (w/w) or more than 50% (w/w) and up to 60% (w/w) of octreotide.

In particular, the one or more additional excipients is a bulking agent, which may be present in a range of 20 to 50% (w/w), preferably 30 to 40% (w/w). More preferred is when the bulking agent is mannitol. Furthermore, the octreotide solid dosage form may have a total moisture content of 5% (w/w) or less, preferably between 2 and 3% (w/w). All weights are based on the total weight of the solid dosage form. The octreotide solid dosage form may have at least one pointed end and an elongate body and it will be appreciated that the solid dosage form may have any of the weight and dimensions described herein.

Alternatively, the solid dosage forms of the invention may comprise PTH 1-34 as the therapeutic peptide. The PTH 1-34 solid dosage form will further comprise CMC and one or more of the additional excipients described herein. For example, the solid dosage form may comprise between 0.1 and 5 weight %, preferably 0.5 to 2.5% (w/w) of PTH 1-34, in addition to 5 to 20% (w/w), preferably 7 to 15% (w/w) of CMC and 80 to 99% (w/w), preferably 85 to 95% (w/w) of one or more additional excipients. In particular, the one or more additional excipients is a bulking agent, which may be present in a range of 20 to 60% (w/w). The bulking agent may be mannitol and/or dextran. Furthermore, the PTH 1-34 solid dosage form may have a total moisture content of 5% or less (w/w), preferably between 2 and 3% (w/w). All weights are based on the total weight of the solid dosage form. The PTH 1-34 solid dosage form may have at least one pointed end and an elongate body and it will be appreciated that the solid dosage form may have any of the weight and dimensions described herein.

Alternatively, the solid dosage forms of the invention may comprise exenatide as the therapeutic peptide. The exenatide solid dosage form will further comprise CMC and one or more of the additional excipients described herein. For example, the solid dosage form may comprise between 0.1 and 5 weight %, preferably 0.2 to 2.5% (w/w) of exenatide, in addition to 5 to 20% (w/w), preferably 7 to 15% (w/w) of CMC and 80 to 99% (w/w), preferably 85 to 95% (w/w) of one or more additional excipients. In particular, the one or more additional excipients is a bulking agent, which may be present in a range of 20 to 60% (w/w). The bulking agent may be mannitol and/or dextran. Furthermore, the exenatide solid dosage form may have a total moisture content of 5% or less (w/w), preferably between 2 and 3% (w/w). All weights are based on the total weight of the solid dosage form. The exenatide solid dosage form may have at least one pointed end and an elongate body and it will be appreciated that the solid dosage form may have any of the weight and dimensions described herein.

Ideally all excipients used are approved for parenteral administration or Generally Regarded As Safe (GRAS).

The solid dosage form of the invention provides a release profile that is substantially bioequivalent to the release profile of an active material administered with a standard needle and syringe.

The rate of release of the active ingredient from a formulation will, to some extent, depend of the solubility of the active ingredient. The solid dosage form may comprise a slow dissolving active ingredient or excipient that also produces a controlled release of the active ingredient to the systemic circulation. The therapeutic peptide may be chosen for its particular release profile.

The addition of one or more disintegrants or controlled release agents to the formulation may be advantageous. Suitable disintegrants and controlled release agents will be known to the skilled person.

The blends of excipients of this invention are used in amounts ranging from 50 to 99.99%, preferably 90% to 99.95%, based on the total weight of the solid dosage form.

Blends of excipients can be prepared as dry mixtures or by combining aqueous solutions or by adding one of the two to an aqueous solution of the other.

The solid dosage may be formed from a bulk preparation comprising a dried matrix in combination with one or more excipients. The dried matrix comprises the therapeutic peptide in combination with one or more excipients, e.g. mannitol. The dried matrix may comprise up to 80% (w/w) of therapeutic peptide, for example, between 1 and 80% (w/w), based on the total weight of the dried matrix. The remaining mass of the dried matrix is made up of one or more excipients, for example, stabilisers, which can help to stabilise the therapeutic protein.

The bulk preparation may comprise up to 90% (w/w) of the dried matrix. For example, the bulk preparation may comprise between 10 to 90% (w/w), 20 to 80% (w/w), 25 to 75% (w/w) or 30 to 65% (w/w) of the dried matrix with the remaining mass being made up of CMC and one or more additional excipients. Thus, if the dried matrix comprises 80% peptide and 90% of the dried matrix is used in the final bulk preparation formulation, the remaining being made up of CMC and other excipients, the final composition of the solid dosage form will comprise 72% peptide. However, if only 75% of the same dried matrix blend is utilised the final composition, the solid dosage form will comprise 60% peptide.

The solid dosage may be formed from a bulk preparation comprising a freeze dried matrix in combination with one or more excipients. The freeze dried matrix comprises the therapeutic peptide in combination with one or more excipients. The freeze dried matrix may comprise up to 80% (w/w) of therapeutic peptide, for example, between 1 and 20% (w/w), based on the total weight of the freeze dried matrix. The remaining mass of the freeze dried matrix is made up of one or more excipients, for example, stabilisers, which can help to stabilise the therapeutic protein.

The bulk preparation may comprise up to 90% (w/w) of the freeze dried matrix. For example, the bulk preparation may comprise between 10 to 90% (w/w), 20 to 80% (w/w), 25 to 75% (w/w) or 30 to 65% (w/w) of the freeze dried matrix with the remaining mass being made up of CMC and optionally one or more additional excipients.

Generally, solid dosage forms of the present invention will have a total weight of less than 10 mg, usually less than 5 mg, for example from 1 mg to 5 mg, particularly in the range of 1.8 to 3.2 mg.

Preferably the solid dosage forms comprises between 0.01 and 50% (w/w) of therapeutic peptide, more preferably, between 0.05 and 30% (w/w), based on the total weight of the solid dosage form. The weight of the active material may be in the range of 3 µg to 1.5 mg. Particular weights of active material include 1 mg, 0.5 mg, 100 µg, 50 µg, 20 µg, 10 µg and 3 µg or any range therebetween.

The term, 'solid dosage form' refers to a dosage form which is neither a liquid, nor a powder e.g. a freeze-dried powder, but is in the form of a solid formulation.

Solid dosage forms of the present invention include rods, pellets, grains, granules and splinters. The cross section may be circular, substantially circular, ellipsoid, triangular, square, or polygonal or a combination of these. The three-dimensional shape of the solid dosage forms may be cylindrical, conical or polyhedral, such as in the form of a cuboid, prism or pyramid, or a combination of these. Preferably the solid dosage forms will have at least one pointed end to facilitate skin penetration. The pointed end may be formed as a cone or bevelled tip formed from two or more intersecting surfaces akin to a chisel, for example.

When two surfaces meet at a common point (vertex) the angle between them, the included angle, is particularly between 10 and 110°, particularly 10 and 90°, yet more particularly between 20 and 65° or between 40° and 60°. Where the tip is in the form of a cone, the top radius of the tip is preferably below half of the diameter of the composition as such, more preferably below a fourth of the diameter of the composition as such.

Preferably the solid dosage formulations of the present invention are crystalline rather than amorphous or glassy. In certain instances, the solid dosage forms may have or will comprise rough surfaces or have a particular surface geometry that imparts a surface texture to the dosage form. In other words, they will not be smooth and featureless in the manner of a glass surface.

The solid dosage forms of the invention may have disintegration times ranging from 30 seconds to 1 day. The combination of excipients in the solid dosage form may be modified to alter disintegration time.

To exert an optimal therapeutic action an active moiety should be delivered to its site of action in an effective concentration for the desired period. To allow reliable prediction of the therapeutic effect the performance of the dosage form containing the active substance should be well characterised.

Preferably the solid dosage forms of the invention are administered using a technology that enables a repeatable dose of drug every administration, regardless of the skin type or location. Suitable delivery systems are disclosed in the Applicant's previous applications published as WO03/023773, WO04/014468 and WO06/082439, herein incorporated by reference. For example, the solid dosage forms of the invention are administered at and penetrate the skin at a low velocity. Particularly, the solid dosage forms are travelling at a low velocity before contacting and penetrating the skin.

The solid dosage forms of the present invention may be formed by methods known in the art.

Briefly, the solid dosage forms of the invention may be produced by a method comprising the following steps:
 (a) blending together dried therapeutic peptide, CMC and one or more additional excipients to create a blend;
 (b) adding water to the blend to make a paste (either before or during extrusion);
 (c) extruding the paste to form an extruded product;
 (d) drying the extruded product;
 (e) cutting the extruded product to form a solid dosage form.

Instead of extruding the paste, the paste may be moulded or formed prior to drying. Alternatively, the paste may be both extruded and moulded prior to drying or the paste may be both extruded and formed prior to drying. Alternatively, the blended dried therapeutic peptide, CMC and one or more additional excipient (each in powder form) may be compressed into form.

The above method can be more fully described as follows:
 1) The therapeutic peptide is freeze dried to produce a freeze dried matrix. One or more of the additional excipients can also be freeze dried with the therapeutic peptide;
 2) The freeze dried matrix is then added to CMC, and optionally one or more of the additional excipients, and then blended;
 3) The blend is mixed with water in a twin screw extruder with a die of the required diameter to produce an extrudate;
 4) The extrudate is cut in to rods and dried in a convection oven. The rods may be dried for about 1 to 5 hours, for example about 3 hours. The convection oven may be at a temperature of about 30 to 60° C., for example about 50° C. Preferably, the rods are dried in a convection oven for about 3 hours at a temperature of about 50° C.; 5) The rods are then dried in a vacuum oven at a temperature of about 30° C. to 70° C., preferably 60° C., until a suitable compressive strength is reached, i.e. a compressive strength of at least 80 MPa. The resulting dried rods are substantially dry.
 6) The rods are further cut to form individual dosage forms of desired length, e.g. from 2 to 6 mm.

A correlation has been noticed such that the lower the level of moisture in the dried dosage form, the higher the compressive strength of the dosage form.

EXAMPLES

The following examples disclose solid dosage forms of the present invention as described above.

Example 1

Octreotide Formulation

Component mixture used to prepare freeze dried matrix (FDM):

| Excipient | % w/w of mixture | % w/w of bulk preparation |
|---|---|---|
| Octreotide acetate | 12.8 | 3.87 |
| Mannitol | 40.77 | 12.33 |
| Histidine | 18.29 | 5.53 |
| Methionine | 18.29 | 5.53 |
| Citric acid | 9.85 | 2.98 |

Bulk preparation:

| Excipient | % w/w of bulk preparation |
|---|---|
| FDM | 30.25% |
| CMC | 35% |
| Mannitol | 34.75% |

The octreotide solid dosage forms were produced by the following method:
1. Octreotide was freeze dried with the stabilising agents (histidine, methionine and citric acid) and mannitol as a bulking agent, to produce a freeze dried matrix;
2. The freeze dried matrix (30.25% w/w) was added to CMC (35% w/w) and mannitol (35.75% w/w) and bag blended to produce a blend;
3. The blend was mixed with water in a twin screw extruder with a die of the required diameter to produce an extrudate;
4. The extrudate was cut into long rods (about 10 cm in length) and dried for 3 hours in a convection oven at 50° C.;
5. The rods were then further dried in a vacuum oven at 60° C. until a suitable compressive strength was reached;
6. The rods were further cut to form individual dosage forms of 4 mm in length.

This method produced dosage forms with a compressive strength of >130 MPa when vacuum dried for at least 48 hours.

TABLE 1

Drying Data for Octreotide

| Time in +50° C. vacuum oven (hours) | Moisture content (%) | Compressive strength (MPa) |
|---|---|---|
| 0 | 6.0 | 52 |
| 24 | 3.8 | 117 |
| 48 | 2.9 | 139 |
| 72 | 1.7 | 145 |
| 96 | 1.4 | 154 |
| 114 | 1.0 | 168 |

To obtain the drying data in Table 1, step 6 of the method above was carried out after varying drying times in the vacuum oven (step 5) and dosage forms of 2 mm in length (rather than 4 mm) were obtained as compressive strength is tested on 2 mm samples. To measure compressive strength, the 2 mm long octreotide samples were compressed between two metal plates and the force required to break the sample was measured and recorded. The data in Table 1 show that as the moisture in the product, as measured by thermogravimetric analysis (TGA), is reduced as the compressive strength increases. When measuring the moisture by TGA, the weight loss of each sample during a temperature ramp is monitored.

Example 2

PTH 1-34 Formulation

Component mixture used to produce freeze dried matrix (FDM):

| Excipient | % w/w of mixture | % w/w of bulk preparation |
|---|---|---|
| PTH 1-34 | 2.66 | 0.93 |
| Mannitol | 65.74 | 22.95 |
| Histidine | 16.64 | 5.82 |
| Methionine | 0.78 | 0.27 |
| EDTA | 1.22 | 0.43 |
| NaOH | 1.83 | 0.64 |
| Cysteine | 7.42 | 2.60 |
| Citric acid monohydrate | 3.71 | 1.31 |

Bulk preparation:

| Excipient | % w/w of bulk preparation |
|---|---|
| FDM | 35% |
| CMC | 10% |
| Mannitol | 24% |
| Dextran | 30% |
| Tween 20 | 1% |

The PTH 1-34 solid dosage forms were produced by the following method:
1. PTH 1-34 was freeze dried with the stabilising agents (histidine, methionine, EDTA, NaOH, cycstein and citric acid monohydrate) and mannitol as a bulking agent, to produce a freeze dried matrix;
2. The freeze dried matrix (35% w/w) was added to CMC (10% w/w), mannitol (24%), Dextran (30% w/w) and Tween 20 (1% w/w) and bag blended to produce a blend;
3. The blend was mixed with water in a twin screw extruder with a die of the required diameter to produce an extrudate;
4. The extrudate was cut into rods and dried for 3 hours in a convection oven at 50° C.;
5. The rods were then further dried in a vacuum oven at 60° C. until a suitable compressive strength was reached;
6. The rods were further cut to form individual dosage forms of 4 mm in length.

This method produced dosage forms with a compressive strength of >100 MPa when vacuum dried for at least 41 hours.

TABLE 2

Drying Data for PTH 1-34

| Time in +50° C. vacuum oven (hours) | Moisture content (%) | Compressive strength (MPa) |
|---|---|---|
| 0 | 5.6 | 45 |
| 17 | 3.5 | 97 |
| 23 | 3.5 | 98 |
| 41 | 2.9 | 110 |
| 65 | 2.8 | 117 |
| 72 | 2.7 | 114 |
| 138 | 1.9 | 125 |
| 161 | 1.7 | 122 |
| 185 | 2.2 | 120 |

To obtain the drying data in Table 1, step 6 of the method above was carried out after varying drying times in the vacuum oven (step 5) and dosage forms of 2 mm in length (rather than 4 mm) were obtained as compressive strength is tested on 2 mm samples. To measure compressive strength, the 2 mm long PTH 1-34 samples were compressed between two metal plates and the force required to break the sample as measured and recorded. The data in Table 2 show that as the moisture in the product, as measured by thermogravimetric analysis (TGA), is reduced the compressive strength increases. When measuring the moisture by TGA, the weight loss of each sample during a temperature ramp is monitored.

Example 3

Exenatide Formulation

Component mixture used to produce freeze dried matrix (FDM):

| Excipient | % w/w of mixture | % w/w of bulk preparation |
| --- | --- | --- |
| Exenatide | 1.50 | 0.50 |
| Mannitol | 70.50 | 24.70 |
| Histidine | 16.60 | 5.81 |
| Methionine | 0.77 | 0.27 |
| EDTA | 1.40 | 0.49 |
| NaCl | 1.83 | 0.64 |
| Cysteine | 7.40 | 2.59 |

Bulk preparation:

| Excipient | % w/w of bulk preparation |
| --- | --- |
| FDM | 35% |
| CMC | 10% |
| Mannitol | 25% |
| Dextran | 30% |

The exenatide solid dosage forms were produced by the following method:

Exenatide was freeze dried with the stabilising agents (histidine, methionine, EDTA, NaCl and cysteine) and mannitol as a bulking agent, to produce a freeze dried matrix;

The freeze dried matrix (35% w/w) was added to CMC (10% w/w), mannitol (25%), Dextran (30% w/w) and bag blended to produce a blend;

The blend was mixed with water in a twin screw extruder with a die of the required diameter to produce an extrudate;

The extrudate was cut into rods and dried for 3 hours in a convection oven at 50° C.;

The rods were then further dried in a vacuum oven at 60° C. until a suitable compressive strength was reached;

The rods were further cut to form individual dosage forms of 4 mm in length.

Example 4

Octreotide Formulation

Component mixture used to prepare dried matrix (DM):

| Excipient | % w/w of mixture | % w/w of bulk preparation |
| --- | --- | --- |
| Octreotide acetate | 80 | 72 |
| Mannitol or alternative excipient | 20 | 18 |

Bulk preparation:

| Excipient | % w/w of bulk preparation |
| --- | --- |
| DM | 90 |
| CMC | 5 |
| Mannitol | 5 |

1. Octreotide (80%) was dried with excipients (20%)—mannitol with one or more further optional excipients within that 20%, to produce a dried matrix (100%)
2. The dried matrix (90% w/w) was added to CMC (5% w/w) and mannitol (5% w/w) and bag blended to produce a solid dosage form blend (100% w/w—total formulation) with 72% peptide.

Example 5

Liraglutide Formulation

Component mixture used to prepare dried matrix (DM):

| Excipient | % w/w of mixture | % w/w of bulk preparation |
| --- | --- | --- |
| Liraglutide | 80 | 60 |
| Mannitol or alternative excipient | 20 | 15 |

Bulk preparation:

| Excipient | % w/w of bulk preparation |
| --- | --- |
| DM | 75 |
| CMC | 20 |
| Mannitol | 5 |

1. Liraglutide (80%) was dried with excipients (20%)—mannitol with one or more optional excipients within that 20%, to produce a dried matrix (100%)
2. The dried matrix (90% w/w) was added to CMC (5% w/w) and mannitol (5% w/w) and bag blended to produce a solid dosage form blend (100% w/w—total formulation) with 60% peptide.

The invention claimed is:

1. A solid dosage form for needle-free injection having a moisture content of between 1 and 5% (w/w), the solid dosage form comprising:
    a dried matrix including at least a first excipient and 0.01 to 50% (w/w) of a therapeutic protein; and
    one or more additional excipients and 5 to 95% (w/w), based on the total weight of the solid dosage form, of carboxymethylcellulose (CMC) blended in the dosage form, wherein the dosage form has a width of 0.5 mm to 2 mm, wherein the compressive strength of the dosage form is at least 80 MPa and is 168 MPa or less.

2. A solid dosage form according to claim 1, wherein the moisture content is between 2% and 3% (w/w).

3. A solid dosage form according to claim 1, wherein the first excipient and/or at least one or more additional excipients is a bulking agent.

4. A solid dosage form according to claim 3, wherein the bulking agent is a polyol.

5. A solid dosage form according to claim 4, wherein the bulking agent is mannitol.

6. A solid dosage form according to claim 1, wherein the protein is a peptide.

7. A solid dosage form according to claim 1, wherein the width of the dosage form is from 0.50 to 1 mm.

8. A solid dosage form according to claim 1, wherein the length of the dosage form is from 2 to 6 mm.

9. A solid dosage form according to claim 1, wherein the total weight of the solid dosage form is from 1 to 5 mg.

10. A solid dosage form according to claim 6, wherein the peptide is octreotide and for use in the treatment or prevention of intestinal tumours or metastatic carcinoid tumours or acromegaly.

11. A solid dosage form according to claim 6, wherein the peptide is PTH or a fragment thereof for use in the treatment of solitary bone cysts or hypoparathyroidism.

12. A solid dosage form according to claim 6, wherein the peptide is exenatide or liraglutide for use in the treatment or prevention of diabetes mellitus type 2.

13. A drug delivery device or packaged drug for use with a drug delivery device which comprises a solid dosage form according to claim 1.

14. A method of treating intestinal tumours, metastatic carcinoid tumours, acromegaly, solitary bone cysts, hypoparathyroidism or diabetes mellitus type 2, said method comprising administering to a subject in need a therapeutically effective amount of a solid dosage form as defined in claim 1.

15. A solid dosage form according to claim 6, wherein the peptide is octreotide, PTH 1-34, exenatide or liraglutide.

16. A solid dosage form according to claim 8, wherein the width of the dosage is 0.85 mm.

17. A solid dosage form according to claim 9, wherein the length of the dosage form is 4 mm.

18. A solid dosage form according to claim 10, wherein the compressive strength of the dosage form is at least 100 MPa.

* * * * *